US012576279B2

(12) United States Patent
Lee et al.

(10) Patent No.: US 12,576,279 B2
(45) Date of Patent: Mar. 17, 2026

(54) HEADER FOR A NEUROSTIMULATOR

(71) Applicant: Axonics, Inc., Irvine, CA (US)

(72) Inventors: Henry Lee, Irvine, CA (US); Prabodh Mathur, Laguna, CA (US); David Marvicsin, Irvine, CA (US); John Miller, Irvine, CA (US); Darin Shirakata, Irvine, CA (US); Arun Venkatasubramanian, Singapore (SG); Ranga Jegadeesan, Singapore (SG)

(73) Assignee: Axonics, Inc., Irvine, CA (US)

( * ) Notice: Subject to any disclaimer, the term of this patent is extended or adjusted under 35 U.S.C. 154(b) by 512 days.

(21) Appl. No.: 18/092,829

(22) Filed: Jan. 3, 2023

(65) Prior Publication Data

US 2023/0211167 A1      Jul. 6, 2023

Related U.S. Application Data

(60) Provisional application No. 63/296,153, filed on Jan. 3, 2022.

(51) Int. Cl.
*A61N 1/375*          (2006.01)
*A61N 1/05*            (2006.01)
(Continued)

(52) U.S. Cl.
CPC ............. *A61N 1/3754* (2013.01); *A61N 1/05* (2013.01); *A61N 1/36175* (2013.01); *A61N 1/37229* (2013.01)

(58) Field of Classification Search
CPC .... A61N 1/3754; A61N 1/05; A61N 1/36175; A61N 1/37229; A61N 1/36071;
(Continued)

(56) References Cited

U.S. PATENT DOCUMENTS

| | | | |
|---|---|---|---|
| 5,363,114 A | 11/1994 | Shoemaker | |
| 5,697,958 A | 12/1997 | Paul et al. | |
| | (Continued) | | |

FOREIGN PATENT DOCUMENTS

| | | |
|---|---|---|
| CA | 2 559 087 A1 | 9/2005 |
| EP | 1 479 087 B1 | 7/2010 |
| | (Continued) | |

OTHER PUBLICATIONS

Cynthia Furse et al., "Design of Implantable Antennas for Communication with Medical Implants"; Soontornpipit Pichitpong, Master of Science; Utah State University; ProQuest Dissertations Publishing; 2002. 1408274.

(Continued)

*Primary Examiner* — Paula J Stice

(74) *Attorney, Agent, or Firm* — Seager Tufte & Wickhem, LLP

(57) ABSTRACT

An implantable pulse generator (IPG) including a case containing an energy storage device and one or more electrode leads. A header is coupled to the case. The header includes a cassette, an antenna coupled to the cassette and electrically coupled to the case, the case configured as a part of the antenna for receiving and transmitting electromagnetic signals, and an electrode attachment structure configured to couple with the cassette and configured to couple with the one or more electrode leads.

26 Claims, 16 Drawing Sheets

(51) Int. Cl.
    *A61N 1/36*      (2006.01)
    *A61N 1/372*    (2006.01)

(58) Field of Classification Search
    CPC .. A61N 1/36125; A61N 1/375; A61N 1/3752;
                     A61N 1/3758; A61N 1/3787
    See application file for complete search history.

(56) References Cited

U.S. PATENT DOCUMENTS

| | | | |
|---|---|---|---|
| 5,861,019 A | 1/1999 | Sun et al. | |
| 6,115,634 A | 9/2000 | Donders et al. | |
| 6,765,779 B2 | 7/2004 | Stevenson et al. | |
| 6,888,715 B2 | 5/2005 | Stevenson et al. | |
| 6,985,347 B2 | 1/2006 | Stevenson et al. | |
| 7,012,192 B2 | 3/2006 | Stevenson et al. | |
| 7,035,076 B1 | 4/2006 | Stevenson | |
| 7,038,900 B2 | 5/2006 | Stevenson et al. | |
| 7,047,076 B1 | 5/2006 | Li et al. | |
| 7,110,823 B2 | 9/2006 | Whitehurst et al. | |
| 7,113,387 B2 | 9/2006 | Stevenson et al. | |
| 7,136,273 B2 | 11/2006 | Stevenson et al. | |
| 7,167,749 B2 | 1/2007 | Biggs et al. | |
| 7,199,995 B2 | 4/2007 | Stevenson et al. | |
| 7,310,216 B2 | 12/2007 | Stevenson et al. | |
| 7,317,946 B2 | 1/2008 | Twetan et al. | |
| 7,535,693 B2 | 5/2009 | Stevenson et al. | |
| 7,554,493 B1 | 6/2009 | Rahman | |
| 7,623,335 B2 | 11/2009 | Stevenson et al. | |
| 7,736,191 B1 * | 6/2010 | Sochor | H01R 24/58 607/116 |
| 7,771,838 B1 | 8/2010 | He et al. | |
| 7,957,806 B2 | 6/2011 | Stevenson et al. | |
| 7,988,507 B2 | 8/2011 | Darley et al. | |
| 8,179,658 B2 | 5/2012 | Brendel et al. | |
| 8,195,295 B2 | 6/2012 | Stevenson et al. | |
| 8,412,339 B2 | 4/2013 | Ok et al. | |
| 8,422,195 B2 | 4/2013 | Stevenson | |
| 8,433,410 B2 | 4/2013 | Stevenson et al. | |
| 8,468,664 B2 | 6/2013 | Brendel et al. | |
| 8,619,002 B2 | 12/2013 | Rawat et al. | |
| 8,653,384 B2 | 2/2014 | Tang et al. | |
| 8,655,453 B2 | 2/2014 | Werder et al. | |
| 8,855,768 B1 | 10/2014 | Johnson et al. | |
| 8,868,189 B2 | 10/2014 | Stevenson et al. | |
| 8,938,309 B2 | 1/2015 | Marzano et al. | |
| 9,014,808 B2 | 4/2015 | Stevenson et al. | |
| 9,064,640 B2 | 6/2015 | Brendel et al. | |
| 9,227,076 B2 | 1/2016 | Sharma et al. | |
| 9,233,253 B2 | 1/2016 | Stevenson et al. | |
| 9,352,150 B2 | 5/2016 | Stevenson et al. | |
| 9,362,660 B2 * | 6/2016 | Ries | H01R 24/58 |
| 9,387,335 B2 * | 7/2016 | Kane | A61N 1/3752 |
| 9,492,659 B2 | 11/2016 | Tang | |
| 9,511,220 B2 | 12/2016 | Marzano et al. | |
| 9,700,731 B2 | 7/2017 | Nassif et al. | |
| 9,770,596 B2 | 9/2017 | Nassif et al. | |
| 9,889,306 B2 | 2/2018 | Stevenson et al. | |
| 9,895,534 B2 | 2/2018 | Stevenson et al. | |
| 9,907,966 B2 | 3/2018 | Funderburk et al. | |
| 9,931,513 B2 | 4/2018 | Kelsch et al. | |
| 9,931,514 B2 | 4/2018 | Frysz et al. | |
| 9,981,137 B2 | 5/2018 | Eiger | |
| 9,993,650 B2 | 6/2018 | Seitz et al. | |
| 10,016,595 B2 | 7/2018 | Stevenson et al. | |
| 10,016,596 B2 | 7/2018 | Stevenson et al. | |
| 10,046,166 B2 | 8/2018 | Stevenson et al. | |
| 10,080,889 B2 | 9/2018 | Marzano et al. | |
| 10,099,051 B2 | 10/2018 | Stevenson et al. | |
| 10,124,164 B2 | 11/2018 | Stevenson et al. | |
| 10,420,949 B2 | 9/2019 | Seitz et al. | |
| 10,500,402 B2 | 12/2019 | Stevenson et al. | |
| 10,583,302 B2 | 3/2020 | Li et al. | |
| 10,587,073 B2 | 3/2020 | Marzano et al. | |
| 10,722,706 B2 | 7/2020 | Stevenson et al. | |
| 10,722,721 B2 | 7/2020 | Nassif et al. | |
| 10,806,937 B2 | 10/2020 | Eiger | |
| 10,857,369 B2 | 12/2020 | Stevenson et al. | |
| 10,869,634 B2 * | 12/2020 | Lim | A61B 5/29 |
| 10,874,866 B2 | 12/2020 | Stevenson et al. | |
| 10,957,970 B2 | 3/2021 | Li et al. | |
| 11,013,928 B2 | 5/2021 | Stevenson et al. | |
| 11,198,014 B2 | 12/2021 | Stevenson et al. | |
| 11,241,581 B2 | 2/2022 | Stevenson et al. | |
| 11,344,734 B2 | 5/2022 | Stevenson et al. | |
| 11,351,387 B2 | 6/2022 | Stevenson et al. | |
| 2002/0123776 A1 | 9/2002 | Von Arx et al. | |
| 2003/0016177 A1 | 1/2003 | Deguchi et al. | |
| 2004/0012535 A1 | 1/2004 | Stone | |
| 2005/0007718 A1 | 1/2005 | Stevenson et al. | |
| 2005/0134520 A1 * | 6/2005 | Rawat | A61N 1/37229 343/873 |
| 2005/0203584 A1 | 9/2005 | Twetan et al. | |
| 2007/0190866 A1 * | 8/2007 | Zart | H01R 43/24 439/736 |
| 2008/0303728 A1 * | 12/2008 | Lee | H01Q 1/243 343/718 |
| 2009/0132007 A1 | 5/2009 | Snitting | |
| 2010/0023000 A1 | 1/2010 | Stevenson et al. | |
| 2012/0052710 A1 * | 3/2012 | Deehr | A61N 1/375 29/874 |
| 2013/0116763 A1 | 5/2013 | Parker et al. | |
| 2013/0150915 A1 * | 6/2013 | Kane | A61N 1/37512 607/36 |
| 2013/0289637 A1 * | 10/2013 | Amely-Velez | A61N 1/3956 607/60 |
| 2013/0309889 A1 * | 11/2013 | Ries | H01R 43/24 29/857 |
| 2014/0002318 A1 | 1/2014 | Meulmester et al. | |
| 2016/0129268 A1 | 5/2016 | Moazen et al. | |
| 2016/0344238 A1 | 11/2016 | Yeh et al. | |
| 2018/0043171 A1 | 2/2018 | Nassif et al. | |
| 2019/0165458 A1 * | 5/2019 | Hartmann-Bax | A61N 1/37229 |
| 2019/0358459 A1 | 11/2019 | Baade et al. | |
| 2020/0324129 A1 | 10/2020 | Nassif et al. | |
| 2021/0167488 A1 | 6/2021 | Li et al. | |
| 2021/0205616 A1 | 7/2021 | Frysz et al. | |
| 2021/0283404 A1 | 9/2021 | Frysz et al. | |

FOREIGN PATENT DOCUMENTS

| | | |
|---|---|---|
| EP | 1 488 434 B1 | 12/2012 |
| EP | 1 126 784 B1 | 1/2013 |
| EP | 1 743 347 B1 | 6/2013 |
| EP | 2 636 427 A1 | 9/2013 |
| EP | 2 269 200 B1 | 9/2014 |
| EP | 2 291 219 B1 | 10/2017 |
| EP | 3 320 950 A1 | 5/2018 |
| EP | 3 345 652 A1 | 7/2018 |
| EP | 3 366 348 A1 | 8/2018 |
| EP | 3 041 572 B1 | 1/2019 |
| EP | 3 449 973 A1 | 3/2019 |
| EP | 3 520 857 A1 | 8/2019 |
| EP | 3 560 553 A1 | 10/2019 |
| EP | 3 838 337 A1 | 6/2021 |
| JP | 2008-537386 A | 9/2008 |
| JP | 2011-500143 A | 1/2011 |
| WO | 2000013585 A1 | 3/2000 |
| WO | 00/25672 A1 | 5/2000 |
| WO | 03/073450 A1 | 9/2003 |
| WO | 2005/087315 A1 | 9/2005 |
| WO | 2006/104847 A1 | 10/2006 |
| WO | 2009/117599 A3 | 9/2009 |

OTHER PUBLICATIONS

Muayad Kod "Wireless Powering and Communication of Implantable Medical Devices"; University of Liverpool; Sep. 2016.

(56)            References Cited

OTHER PUBLICATIONS

International Search Report and Written Opinion dated May 1, 2023
issued in related International Patent Application No. PCT/US2023/
010005; filed Jan. 2, 2023.

* cited by examiner

HEADER FOR A NEUROSTIMULATOR

CROSS-REFERENCE TO RELATED APPLICATIONS

This application claims priority to and the benefit of U.S. Provisional Patent Application No. 63/296,153 entitled NEUROSTIMULATOR SYSTEM filed on Jan. 3, 2022, which is hereby incorporated by reference in its entirety.

BACKGROUND

There is a demand for improvement in antenna systems in implantable neurostimulation devices such as an implantable pulse generator (IPG). Current stimulation systems rely on wireless communication to maintain control of the implantable neurostimulation system. This wireless communication is frequently performed using one or more antennas. Construction of such implantable devices has many difficulties because of the biological environment that they must survive in and because of the compact size requirements. Therefore, needs exist for construction techniques for such devices, which fulfill requirements while maintaining ease of construction and manufacturing.

SUMMARY

One embodiment disclosed herein relates to an implantable pulse generator (IPG). The IPG includes a case containing an energy storage device. A header is coupled to the case. The header includes a cassette, an antenna coupled to the cassette and electrically coupled to the case, the case configured as a part of the antenna for receiving and transmitting electromagnetic signals, and an electrode attachment structure configured to couple with the cassette and configured to couple with one or more electrode leads.

Another disclosed embodiment relates to a header for an implantable biomedical device. The header includes a cassette providing a support structure, an antenna coupled to the cassette and configured to be electrically coupled to a case of the implantable biomedical device, the case configured as a part of the antenna for receiving and transmitting electromagnetic signals. The header also including an electrode attachment structure configured to couple with the cassette and configured to couple with one or more electrode leads.

Yet another disclosed embodiment relates to an implantable pulse generator (IPG). The IPG includes a case containing an energy storage device. The IPG also includes a header coupled to the case. The header include a cassette providing a support structure, an antenna bent at least partially around the cassette and electrically coupled to the case through at least one capacitor, the case configured as a part of the antenna for receiving and transmitting electromagnetic signals, an electrode attachment structure configured to couple with the cassette and configured to couple with one or more electrode leads and an epoxy fill material for sealing the header.

In addition to the foregoing, other aspects are described in the claims, drawings, and text forming a part of the disclosure set forth herein. The foregoing is a summary and thus may contain simplifications, generalizations, inclusions, and/or omissions of detail. Consequently, those skilled in the art will appreciate that the summary is descriptive only and further reference may be made to the drawings and description below for clarification. Other aspects, features, and advantages of the devices and/or processes and/or other subject matter described herein will become apparent upon review of the disclosure set forth herein.

BRIEF DESCRIPTION OF THE DRAWINGS

The use of the same symbols in different drawings typically indicates similar or identical items unless context dictates otherwise.

DETAILED DESCRIPTION

The present application relates to an antenna and header for an IPG, also referred to herein as an "implantable neurostimulator" or a "neurostimulator." The IPG may be a sacral nerve stimulation treatment system configured to treat overactive bladder ("OAB") and relieve symptoms of bladder related dysfunction. However, the devices and systems disclosed herein may also be utilized for a variety of neuromodulation uses, such as fecal dysfunction, and the treatment of pain or other indications, such as movement or affective disorders. The devices and systems disclosed herein may further be used for other implantable devices such as but not limited to pacemakers, deep brain stimulation devices, etc.

Figure 1:
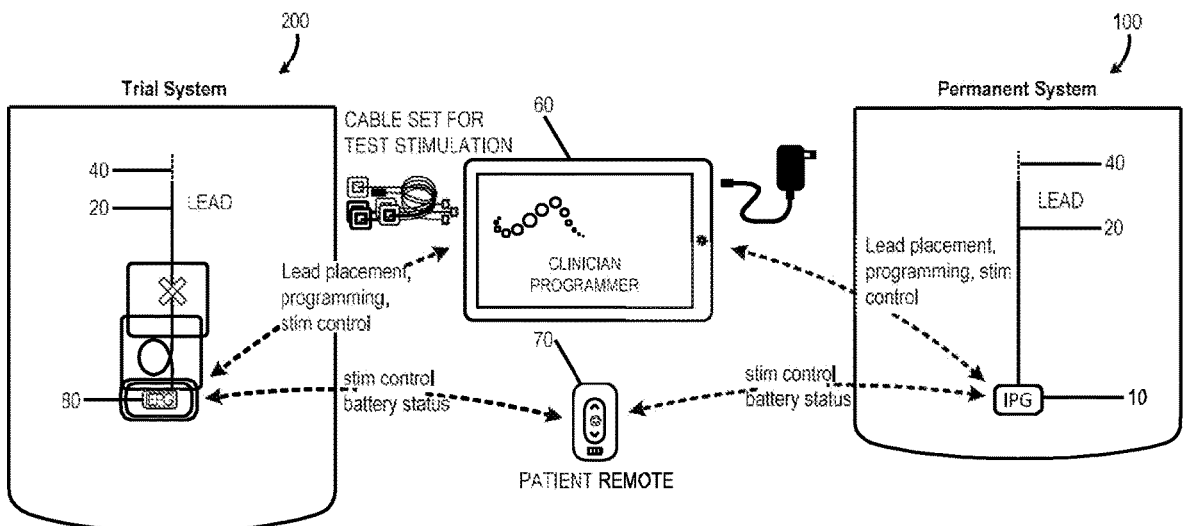
FIG. 1 is a schematic diagram of an illustrative embodiment of a nerve stimulation system, which includes a clinician programmer and a patient remote used in positioning and/or programming of both a trial neurostimulation system and a permanently implanted neurostimulation system.

FIG. 1 schematically illustrates an exemplary nerve stimulation system, which includes both a trial neurostimulation system 200 and a permanently implanted neurostimu-lation system 100. An External Pulse Generator (EPG) 80 and an Implantable Pulse Generator (IPG) 10 are each compatible with and wirelessly communicate with a clini-cian programmer 60 and a patient remote 70, which are used in positioning and/or programming the trial neurostimula-tion system 200 and/or permanently implanted system 100 after a successful trial. Each of IPG 10 and EPG 80 are configured to be connected to leads 20 with nerve stimula-tion electrodes 40 coupled thereto. The clinician program-mer can include specialized software, specialized hardware, and/or both, to aid in lead placement, programming, re-programming, stimulation control, and/or parameter setting. In addition, each of the IPG 10 and the EPG 80 allows the patient at least some control over stimulation (e.g., initiating a pre-set program, increasing or decreasing stimulation), and/or to monitor battery status with the patient remote. This approach also allows for an almost seamless transition between the trial system and the permanent system.

The clinician programmer 60 is used by a physician to adjust the settings of the EPG 80 and/or IPG 10 while the lead 20 is implanted within the patient. The clinician pro-grammer can be a tablet computer or any other computing device used by the clinician to program the IPG 10, or to control the EPG 80 during the trial period. The clinician programmer 60 can also include capability to record stimu-lation-induced electromyograms to facilitate lead placement and programming. The patient remote 70 can allow the patient to turn the stimulation on or off, or to vary stimula-tion from the IPG 10 while implanted, or from the EPG 80 during the trial phase.

The clinician programmer 60 has a control unit which can include a microprocessor and specialized computer code instructions for implementing methods and systems for use by a physician in deploying the treatment system and setting up treatment parameters. The clinician programmer 60 gen-erally includes a user interface which can be a graphical user interface. Other connectors of the clinician programmer 60 may be configured for coupling with an electrical ground or ground patch, an electrical pulse generator (e.g., an EPG 80 or an IPG 10), or the like.

The clinician programmer is configured to operate in combination with an EPG 80 when placing leads in a patient body. The clinician programmer 60 can be electronically coupled to the EPG 80 during test simulation through a specialized cable set. The test simulation cable set can connect the clinician programmer device 60 to the EPG 80 and allow the clinician programmer 60 to configure, modify, or otherwise program the electrodes 40 on the leads 20 connected to the EPG 80.

The electrical pulses generated by the EPG 80 and IPG 10 are delivered to one or more targeted nerves via one or more neurostimulation electrodes 40 at or near a distal end of each of one or more leads 20. The leads 20 can have a variety of shapes, can be a variety of sizes, and can be made from a variety of materials, which size, shape, and materials can be tailored to the specific treatment application. While in this embodiment, the lead is of a suitable size and length to extend from the IPG 10 and through one of the foramen of the sacrum to a targeted sacral nerve, in various other applications, the leads may be, for example, implanted in a peripheral portion of the patient's body, such as in the arms or legs, and can be configured to deliver electrical pulses to the peripheral nerve such as may be used to relieve chronic pain. The leads and/or the stimulation programs may vary according to the nerves being targeted.

Figure 2A:
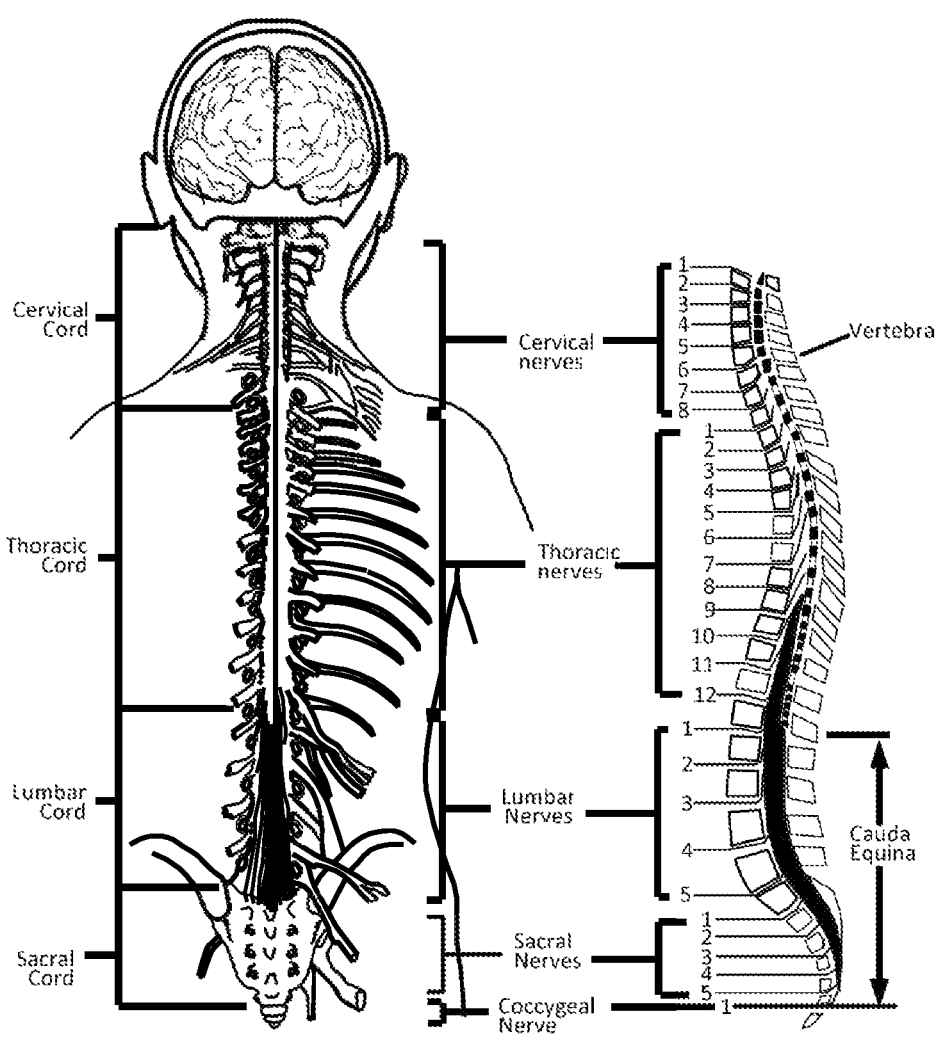
FIGS. 2A-2C are schematic diagrams of illustrative nerve structures along the spine, the lower back and sacrum region.
Figure 2B:
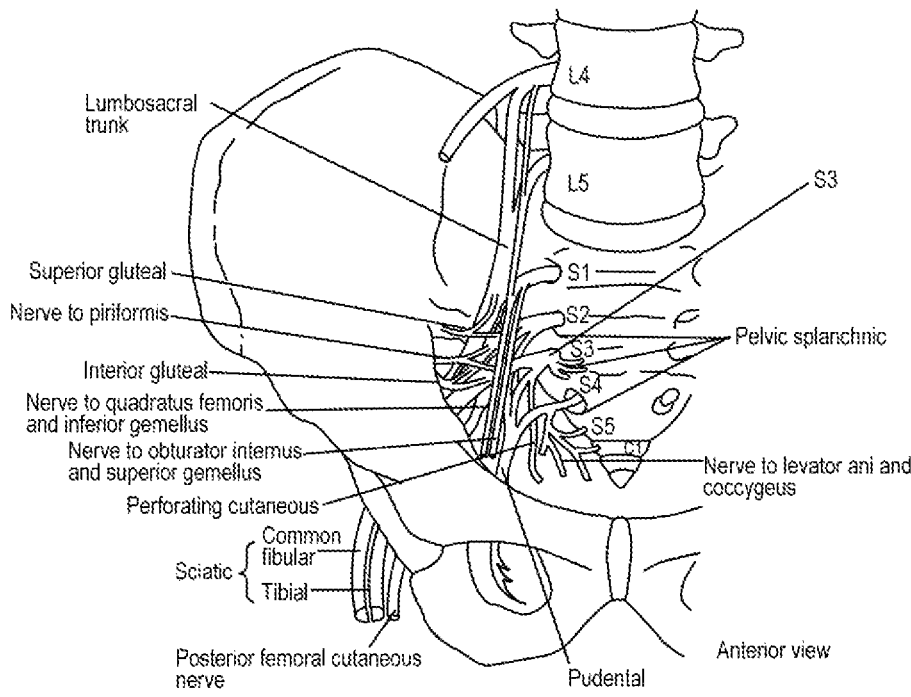
Figure 2C:
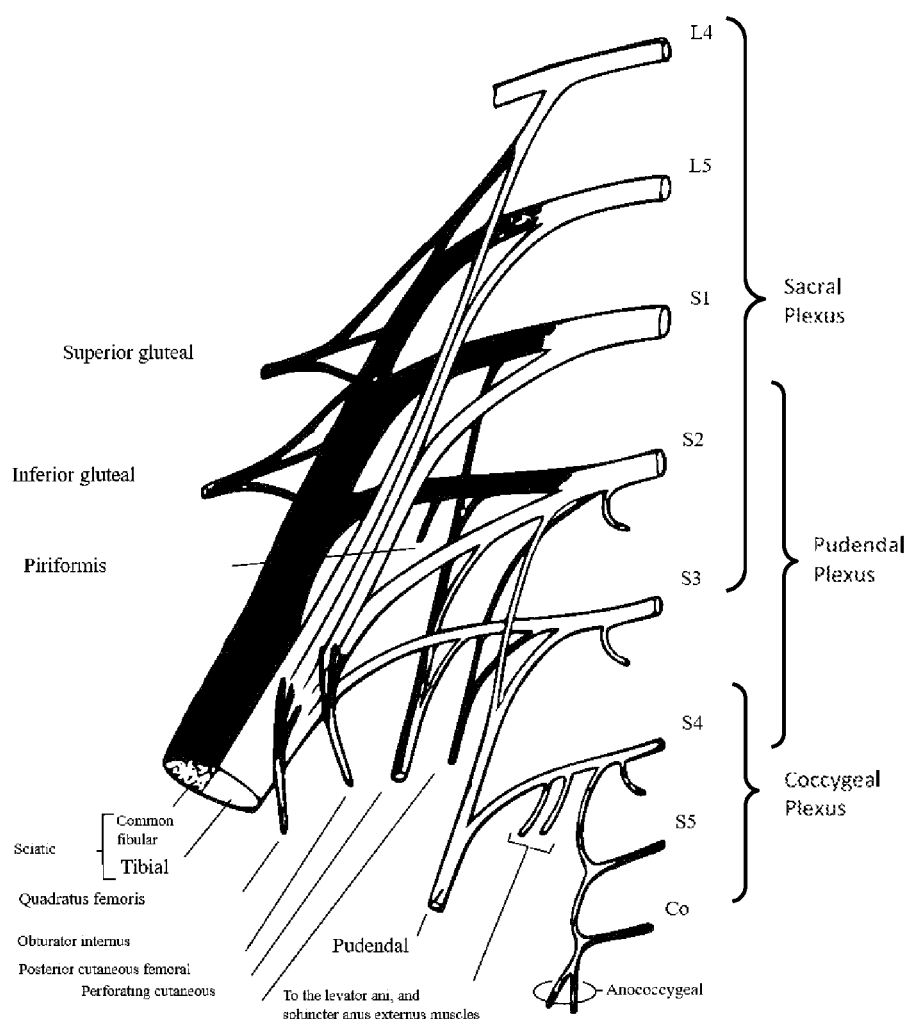

For reference, FIGS. 2A-2C depict diagrams of various nerve structures of a patient, which may be used in neuro-stimulation treatments. FIG. 2A depicts the different sections of the spinal cord and the corresponding nerves within each section. The spinal cord is a long, thin bundle of nerves and support cells that extend from the brainstem along the cervical cord, through the thoracic cord and to the space between the first and second lumbar vertebra in the lumbar cord. Upon exiting the spinal cord, the nerve fibers split into multiple branches that innervate various muscles and organs transmitting impulses of sensation and control between the brain and the organs and muscles. Since certain nerves may include branches that innervate certain organs, such as the bladder, and branches that innervate certain muscles of the leg and foot, stimulation of the nerve at or near the nerve root near the spinal cord can stimulate the nerve branch that innervate the targeted organ, which may also result in muscle responses associated with the stimulation of the other nerve branch.

FIG. 2B depicts the nerves associated with the lower back section, in the lower lumbar cord region where the nerve bundles exit the spinal cord and travel through the sacral foramens of the sacrum. In some illustrative embodiments, the neurostimulation lead 20 is advanced through the fora-men until the neurostimulation electrodes are positioned at the anterior sacral nerve root, while the anchoring portion of the lead proximal of the stimulation electrodes are generally disposed dorsal of the sacral foramen through which the lead passes, so as to anchor the lead in position. FIG. 2C depicts a detailed view of the nerves of the lumbosacral trunk and the sacral plexus, in particular, the S1-S5 nerves of the lower sacrum. The S3 sacral nerve is of particular interest for treatment of bladder related dysfunction, and in particular OAB.

Figure 3:
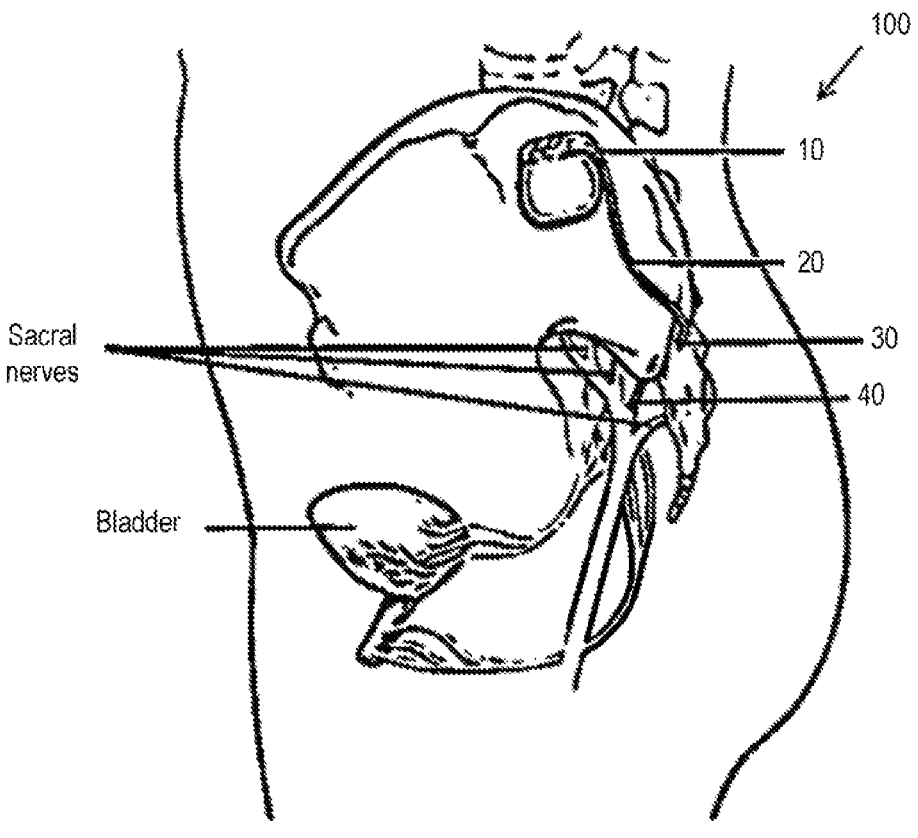
FIG. 3 is a schematic diagram of an illustrative embodiment of a fully implanted neurostimulation system.

FIG. 3 schematically illustrates an example of a fully implanted neurostimulation system 100 adapted for sacral nerve stimulation. Neurostimulation system 100 includes an IPG 10 implanted in a lower back region and connected to a neurostimulation lead 20 extending through the S3 fora-men for stimulation of the S3 sacral nerve. The lead is anchored by a tined anchor portion 30 that maintains a position of a set of neurostimulation electrodes 40 along the targeted nerve, which in this example, is the anterior sacral nerve root S3 which enervates the bladder so as to provide therapy for various bladder related dysfunctions. While this embodiment is adapted for sacral nerve stimulation, similar systems can be used in treating patients with, for example, chronic, severe, refractory neuropathic pain originating from peripheral nerves or various urinary dysfunctions or still further other indications. Implantable neurostimulation sys-tems can be used to either stimulate a target peripheral nerve or the posterior epidural space of the spine.

Properties of the electrical pulses can be controlled via a controller of the implanted pulse generator 10. In some embodiments, these properties can include, for example, the frequency, strength, pattern, duration, or other aspects of the electrical pulses. These properties can include, for example, a voltage, a current, or the like. This control of the electrical pulses can include the creation of one or more electrical pulse programs, plans, or patterns, and in some embodi-ments, this can include the selection of one or more pre-existing electrical pulse programs, plans, or patterns. In the embodiment depicted in FIG. 3, the implantable neurostimu-lation system 100 includes a controller in the IPG 10 having one or more pulse programs, plans, or patterns that may be pre-programmed or created as discussed above. In some embodiments, these same properties associated with the IPG

10 may be used in an EPG 80 of a partly implanted trial system used before implantation of the permanent neurostimulation system 100.

Figure 4:
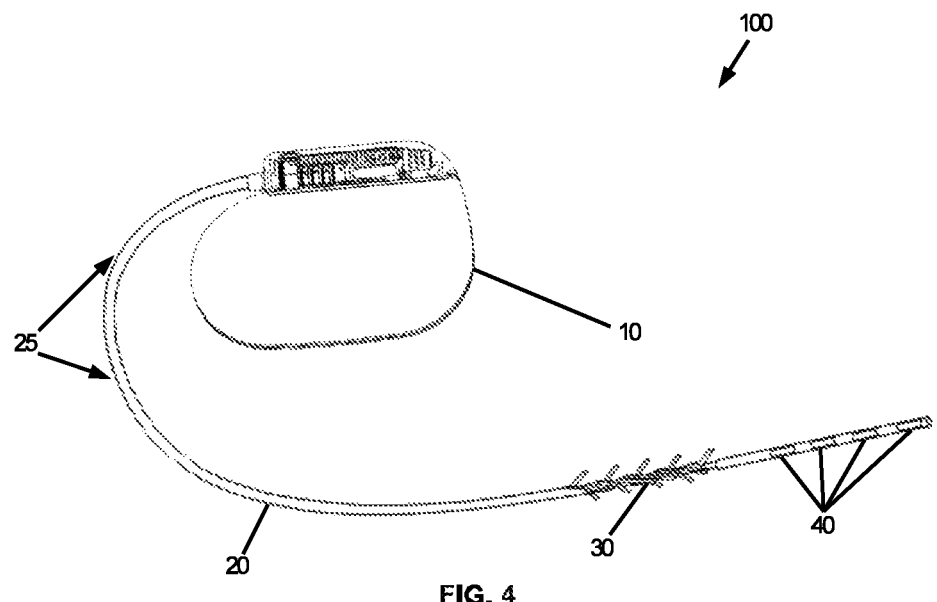
FIG. 4 is a schematic diagram of an illustrative embodiment of a neurostimulation system having an implantable stimulation lead, an implantable pulse generator.

FIG. 4 illustrates an example neurostimulation system 100 that is fully implantable and adapted for sacral nerve stimulation treatment. The implantable system 100 includes an IPG 10 that is coupled to a neurostimulation lead 20 that includes a group of neurostimulation electrodes 40 at a distal end of the lead. The lead includes a lead anchor portion 30 with a series of tines extending radially outward so as to anchor the lead and maintain a position of the neurostimulation lead 20 after implantation. The lead 20 may further include one or more radiopaque markers 25 to assist in locating and positioning the lead using visualization techniques such as fluoroscopy. In some embodiments, the IPG 10 provides monopolar or bipolar electrical pulses that are delivered to the targeted nerves through one or more neurostimulation electrodes, typically, but not limited to four electrodes. In sacral nerve stimulation, the lead is typically implanted through the S3 foramen as described herein.

Figure 5A:
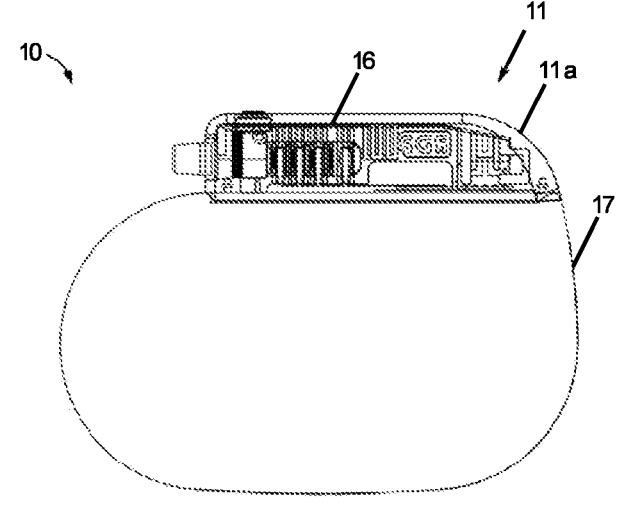
FIG. 5A and 5B are schematic diagrams of an illustrative embodiment of an implantable pulse generator and associated components for use in a neurostimulation system.
Figure 5B:
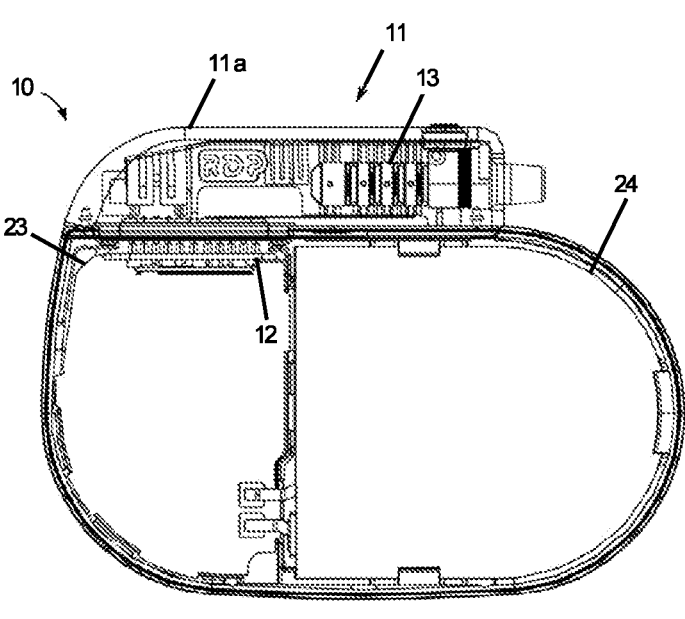

The system 100 may further include a patient remote 70 and clinician programmer 60, each configured to wirelessly communicate with the implanted IPG 10. The clinician programmer 60 may be a tablet computer used by the clinician to program the IPG 10. The patient remote 70 may be a battery-operated, portable device that utilizes radio-frequency (RF) signals to communicate with the IPG 10 and allows the patient to adjust the stimulation levels, check the status of the IPG 10 battery level, and/or to turn the stimulation on or off FIGS. 5A and 5B show detail views of an IPG 10 and its internal components. In some illustrative embodiments, the pulse generator may generate one or more non-ablative electrical pulses that are delivered to a nerve to control pain or cause some other desired effect, for example to inhibit, prevent, or disrupt neural activity for the treatment of OAB or bladder related dysfunction. In some applications, the pulses having a pulse amplitude in a range between 0 mA to 1,000 mA, 0 mA to 100 mA, 0 mA to 50 mA, 0 mA to 25 mA, and/or any other or intermediate range of amplitudes may be used. One or more of the pulse generators may include a controller (e.g. processor) and/or memory adapted to provide instructions to and receive information from the other components of the implantable neurostimulation system. The processor may include a microprocessor, such as a commercially available microprocessor from Intel® or Advanced Micro Devices, Inc.®, or the like. The IPG 10 may include an energy source or energy storage device 24, such as a battery and/or one or more capacitors, and may also include a wireless charging unit.

One or more properties of the electrical pulses may be controlled via a controller of the IPG 10. In some illustrative embodiments, these properties may include, for example, the frequency, strength, pattern, duration, or other aspects of the timing and magnitude of the electrical pulses. These properties may further include, for example, a voltage, a current, or the like. This control of the electrical pulses may include the creation of one or more electrical pulse programs, plans, or patterns, and in some embodiments, this may include the selection of one or more pre-existing electrical pulse programs, plans, or patterns. The IPG 10 includes a controller, also referred to herein as a processor or microprocessor, having one or more pulse programs, plans, or patterns that may be created and/or pre-programmed. In some illustrative embodiments, the IPG 10 may be programmed to vary stimulation parameters including pulse amplitude in a range from 0 mA to 10 mA, pulse width in a range from 50 µs to 500 µs, pulse frequency in a range from 5 Hz to 250 Hz, stimulation modes (e.g., continuous or cycling), and electrode configuration (e.g., anode, cathode, or off), to achieve the optimal therapeutic outcome specific to the patient. In particular, this allows for an optimal setting to be determined for each patient even though each parameter may vary from person to person.

As shown in FIGS. 5A and 5B, the IPG 10 may include a header portion 11. The header portion 11 houses a feedthrough assembly 12, a connector stack 13, and a communication antenna 16 to facilitate wireless communication with the clinician programmer 60 and the patient remote 70. The IPG 10, excluding the header 11, is covered with a titanium case 17, which encases the circuitry 23 including the printed circuit board, memory and controller components that facilitate the electrical pulse programs described above. The titanium case 17 further encompasses an energy storage device 24, which may be a battery. Encapsulating material 11a may be utilized in order to encase at least a portion of the components of the header portion 11.

Figure 10:
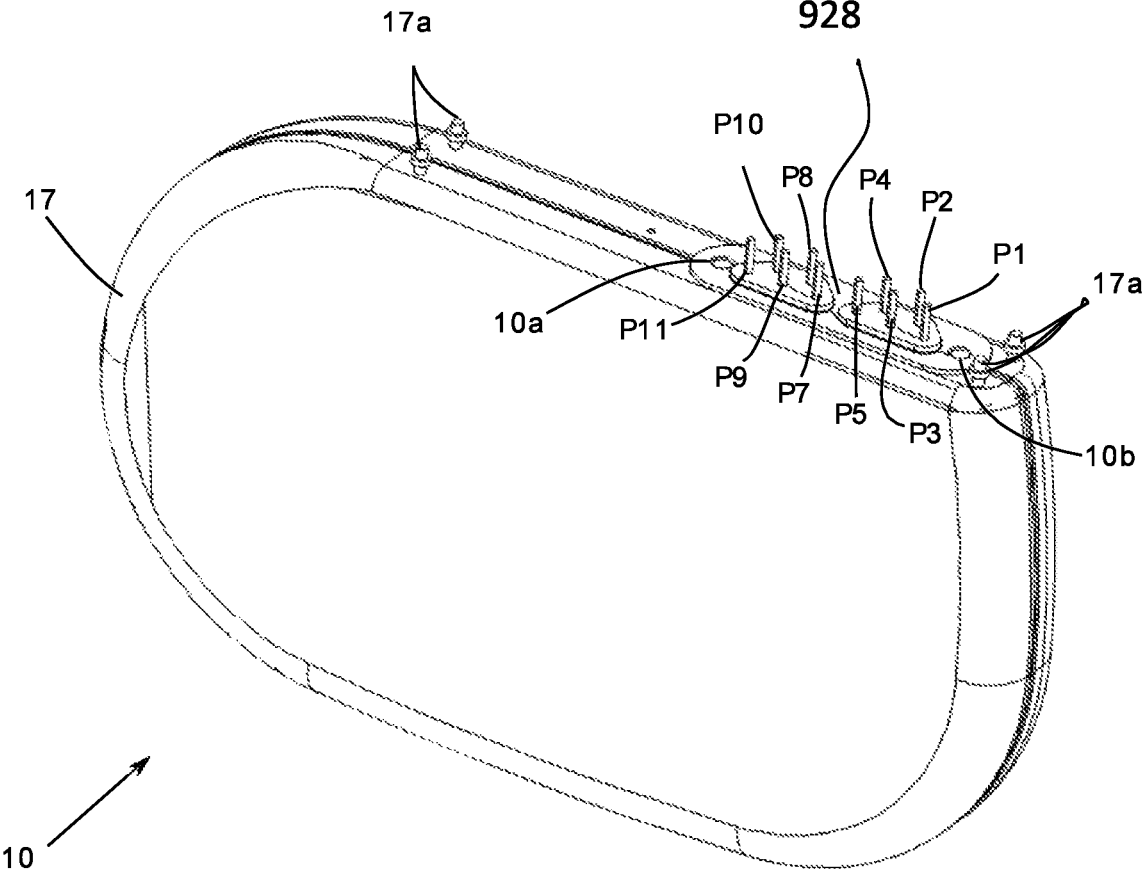
FIG. 10 is an isometric view of an illustrative embodiment of an IPG shown in FIG. 8 without the header.

As shown in FIG. 5B, the feedthrough assembly 12 includes multiple pins that pass through from the case into the header 11. The pins are shown in FIG. 10 protruding upwards from the case. The pins couple to the connector stack 13 in which the proximal end of the lead is coupled. The multiple pins correspond to the four electrodes of the neurostimulation lead. In some embodiments, a Balseal® type connector stack is electrically connected to a plurality of feedthrough pins. The pins may comprise niobium. Alternatively, the pins may be platinum or a platinum/iridium alloy. The pins may be brazed to an alumina ceramic insulator plate along with a titanium alloy flange. The feedthrough assembly may be laser seam welded to a titanium-ceramic brazed case to form a complete hermetic housing for the electronics. Some or all of the pieces of the IPG 10 forming the hermetic housing may be biocompatible, and specifically, may have external surfaces made of biocompatible materials.

Figure 6:
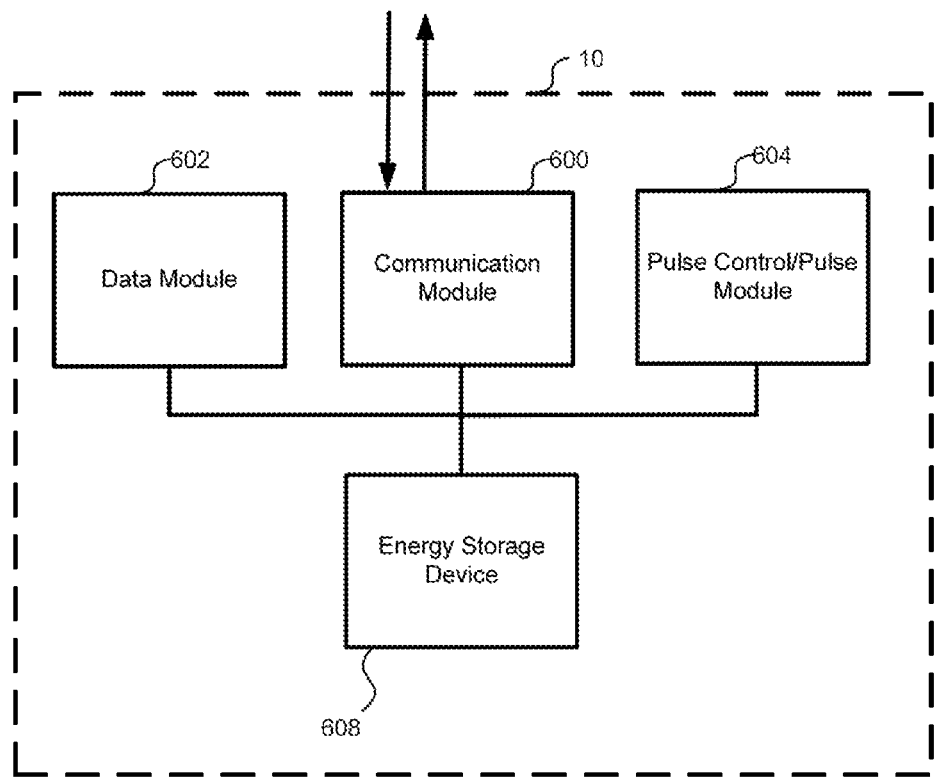
FIG. 6 is a block diagram of an illustrative embodiment of the architecture of an IPG.

FIG. 6 depicts a block diagram schematic illustration of one embodiment of the architecture of the IPG 10. In some embodiments, each of the components of the architecture of the IPG 10 may be implemented using the processor, memory, and/or other hardware component of the IPG 10. In some embodiments, the components of the architecture of the IPG 10 may include software that interacts with the hardware of the IPG 10 to achieve a desired outcome, and the components of the architecture of the IPG 10 may be located within the housing.

The IPG 10 may include a data module 602. The data module 602 may be configured to manage data relating to the identity and properties of the IPG 10. In some embodiments, the data module 602 may include one or several database that may, for example, include information relating to the IPG 10 such as, for example, the identification of the IPG10, one or several properties of the IPG 10, or the like. In accordance with various illustrative embodiments, the data identifying the IPG 10 may include, for example, a serial number of the IPG 10 and/or other identifier of the IPG 10 including, for example, a unique identifier of the IPG 10. In some embodiments, the information associated with a property of the IPG 10 may include, for example, data identifying the function of the IPG 10, data identifying the power consumption of the IPG 10, data identifying the charge capacity of the IPG 10 and/or power storage capacity of the IPG 10, data identifying potential and/or maximum rates of charging of the IPG 10, and/or the like.

The IPG 10 may include a pulse control 604. In accordance with various illustrative embodiments, the pulse control 604 may be configured to control the generation of one or several pulses by the IPG 10. In some embodiments, for example, this may be performed based on information that identifies one or several pulse patterns, programs, or the like. This information may further specify, for example, the frequency of pulses generated by the IPG 10, the duration of pulses generated by the IPG 10, the strength and/or magnitude of pulses generated by the IPG 10, or any other details relating to the creation of one or several pulses by the IPG 10. In accordance with various illustrative embodiments, this information may specify aspects of a pulse pattern and/or pulse program, such as, for example, the duration of the pulse pattern and/or pulse program, and/or the like. In accordance with various illustrative embodiments, information relating to and/or for controlling the pulse generation of the IPG 10 may be stored within the memory.

In accordance with various illustrative embodiments, the pulse module 604 may include stimulation circuitry. The stimulation circuitry may be configured to generate and deliver one or several stimulation pulses, and specifically may be configured to generate a voltage driving a current forming one or several stimulation pulses. This circuitry may include one or several different components that may be controlled to generate the one or several stimulation pulses, to control the one or several stimulation pulses, and/or to deliver the one or several stimulation pulses.

The IPG 10 may include an energy source, such as an energy storage device 608. The energy storage device 608, which may include the energy storage features, may be any device configured to store energy and may include, for example, one or several batteries, capacitors, fuel cells, or the like. The IPG 10 may further include, for example, a communication module 600. The communication module 600 may be configured to send data to and receive data from other components and/or devices of the exemplary nerve stimulation system including, for example, the clinician programmer 60 and/or the patient remote 70. In accordance with various illustrative embodiments, the communication module 600 may connect to one or several antennas 16 and may include software configured to control the one or several antennas to send information to and receive information from one or several of the other components of the IPG 10. While discussed herein in the context of the IPG 10, in accordance with various illustrative embodiments, the communication module 600 as disclosed herein may be supplemented or alternatively located by, for example, the patient remote 70 and/or the clinician programmer 60.

Figure 7:
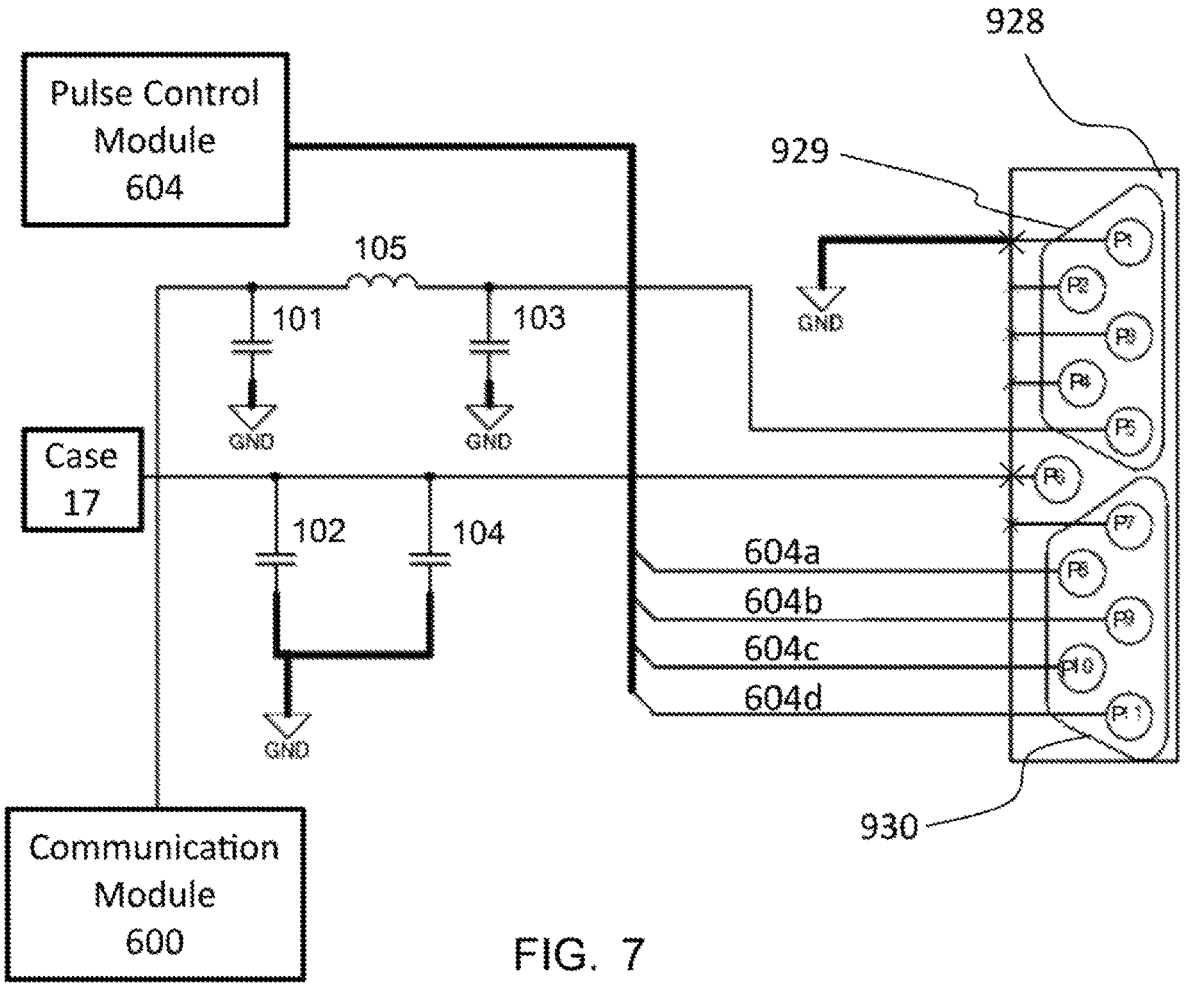
FIG. 7 is a schematic diagram of an illustrative embodiment of an antenna and case ground circuit.

FIG. 7 depicts the antenna circuit within the header 11 of the IPG 10. The header 11 of the implantable nerve stimulator 10 includes an inverted F-type antenna 16. A multi-purpose housing (i.e. case 17) may serve as an electrode during stimulation and as a part of the antenna 16 during communication. The case 17 is coupled to circuit ground via at least one capacitor (e.g., 102 and 104). The capacitors may be configured to function as an open circuit to stimulation pulses and a conductive path (or closed circuit) for communication signals. For example, the capacitor may either function as an open circuit by having a high impedance or as a conductive path (closed circuit) by having little to no impedance. The impedance may be varied by changing the frequency of the electrical signal through the capacitor. The capacitor 102 and the capacitor 104 provide the case 17 an RF ground path allowing the case to be a ground reference for the antenna.

The feedthrough connector plate 928 may include a first riser plate 929 and a second riser plate 930. Each of the riser plates may include a set of capacitively coupled feed through pins. In addition, a separate pin may be provided on the connector plate for connecting to the case. Each of the capacitively coupled feedthrough pins may include a ceramic layer between a metal portion (i.e., core) of the pin and the surrounding metal portions of a feedthrough plate or case (i.e., metal plate of the header). As shown in FIG. 7, certain pins may be connected to the same conductive circuit and the case 17. For example, pins P2, P3, P4 and P7 may be connected to pin P6 via the feedthrough connector plate 928 and, thus, are connected to the case 17 of the IPG 10 and two of the capacitors 102, 104. While each riser plate depicted in the exemplary embodiment shown in FIG. 7 includes a set of five capacitively coupled feed through pins, any number of pins may be used depending upon the use and needs of the IPG 10. In addition, the communication module, pulse control module and case may be connected to one or more of the feed through pins.

The capacitively coupled pins may also provide Magnetic Resonance Imaging (MRI) protection. For example, the presence of a magnetic field may be detected using the signal carried by the pins and the operation of the IPG 10 may be adjusted accordingly during an MRI procedure. For example, the IPG10 may be temporarily shut down during the MRI procedure. As shown in FIG. 7, the capacitors 101, 103 and the inductor 105 may be configured as antenna impedance matching components. The electromagnetic field created during the MRI procedure impacts the inductive coil 105 and may be detected by the communication module.

Pulse control module 604 is configured to be connected to certain of the capacitively coupled feed through pins. For example, as shown in FIG. 7, four of the pins (P8-P11) may each be connected to one of the output lines (604a-604d) of the pulse control module 604. The communication module 600 is configured to be connected to one of the capacitively coupled feed through pins (e.g., P5). The communication module may include a transceiver configured to send and/or receive data to and/or from the antenna in order to communicate with outside devices such as the clinician programmer 60 and/or the patient remote 70.

Figure 8:
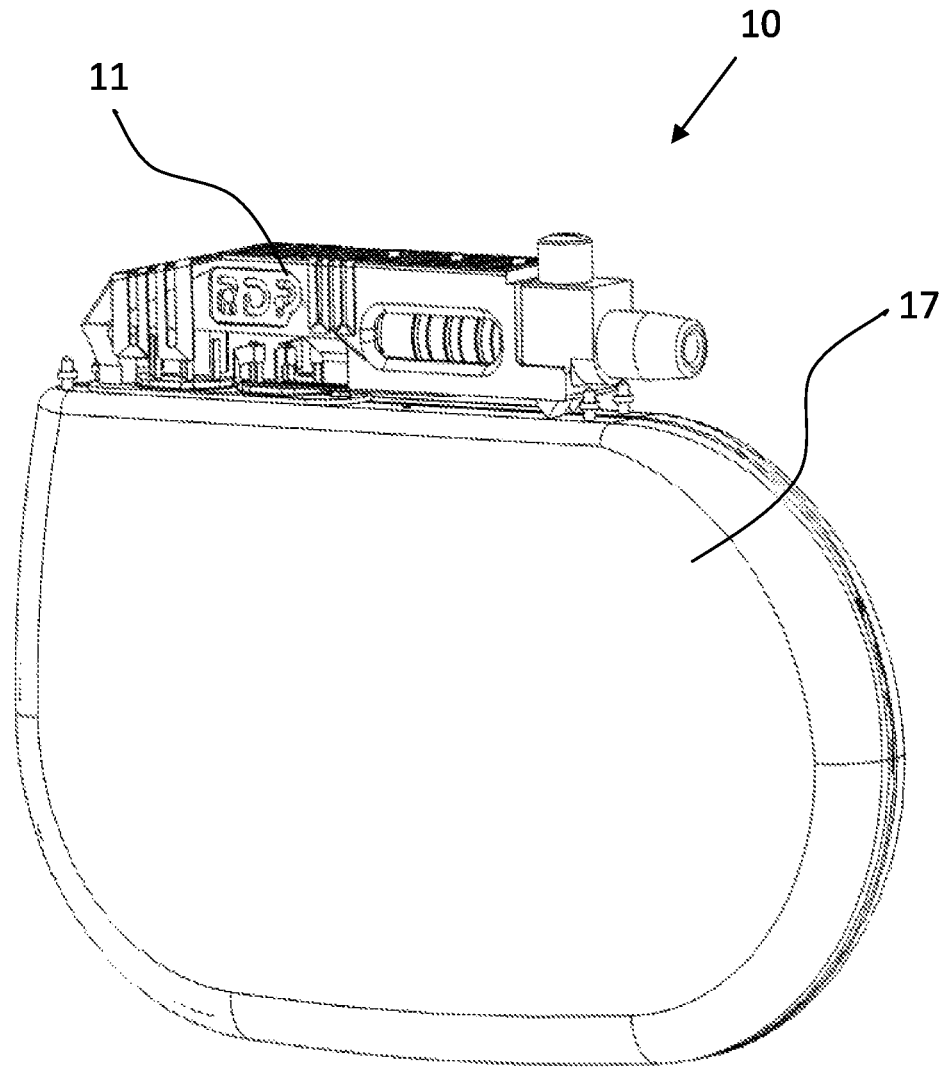
FIG. 8 is a perspective view of an illustrative embodiment of an IPG.

FIG. 8 depicts an isometric view of another embodiment of an IPG 10. The header 11 is encapsulated with a material, typically transparent epoxy, but the encapsulating material is omitted from the view depicted in FIG. 8.

Figure 9:
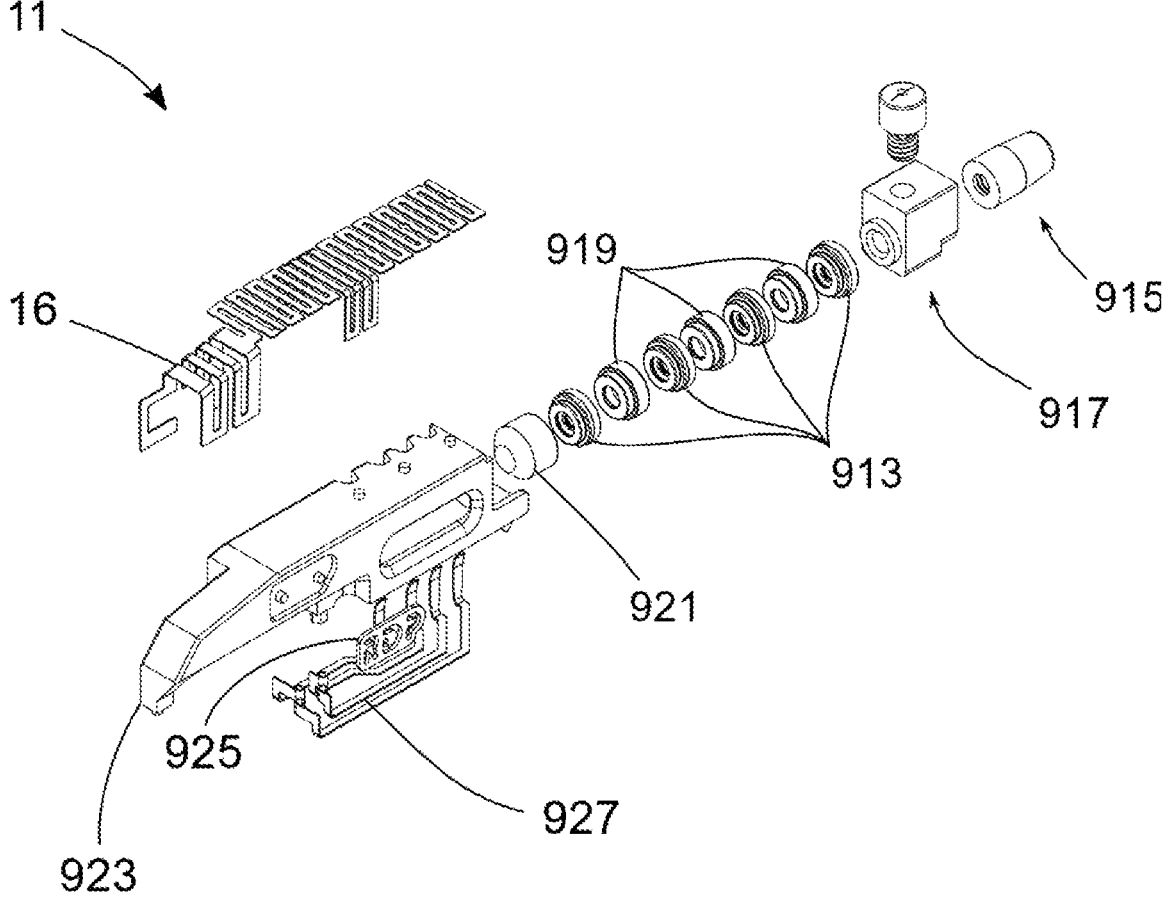
FIG. 9 is an exploded view of an illustrative embodiment of a header of the IPG shown in FIG. 8.

FIG. 9 depicts an illustrative embodiment of the header 11 and an exploded view of its components for the illustrative embodiment shown in FIGS. 5A and 5B. The header 11 may include an antenna 16, strain relief 915, set screw block 917, cassette 923, X-ray identification 925, lead frame 927, and the encapsulating material 11a which surrounds the entire header 11 components. The header also includes the connector stack which includes contact(s) 919, seal(s) 913, and an end cap 921. The X-ray identification 925 is configured to be radiopaque to X-radiation in order to aid in identifying the IPG 10 during an X-ray procedure.

FIG. 10 depicts the case 17 of the IPG 10. The case 17 may include a feedthrough connector plate 928 including the first riser having the first set of capacitively coupled feedthrough pins and the second riser having the second set of feedthrough pins. A separate pin (e.g., P6) may be connected to the feedthrough connector plate 928. Each of the pins may be configured to function as part of a signal carrying circuit for one of the patient electrodes 20, antenna 16, and case 17. For example, certain pins are configured to connect to the antenna 16 while other pins are configured to connect to the lead frame 927. The case 17 may include a first attachment opening 10*a* and a second attachment opening 10*b* configured to attach to the cassette 923. The case may further include holders 17*a* configured to hold the encapsulating material 11*a* when the material solidifies around the header 11 components.

FIG. 11A-11D show different views of an alternative embodiment of a cassette 950 located in the IPG header 11. The cassette 950 is configured to attach to the top of the case 17 of the IPG 10 and provides support for the antenna 16 and other components located in the header 11. The cassette 950 includes a first attachment portion 14 and a second attachment portion 15. The first attachment portion 14 is configured to attach to the first attachment opening 10*a* via interference fit or press fit. The interference fit is configured to hold the first attachment portion 14 of the cassette within the first attachment opening 10*a*. Preferably, the first attachment portion 14 may be configured as a post with a hexagonal cross-section in order to ensure correct alignment of the cassette and the case. However, other shapes and configurations of the first attachment portion may be employed as suitable to ensure a proper alignment and connection between the cassette and the case. The second attachment portion 15 is configured to be positioned within a second attachment opening 10*b* of the case 17. The second attachment portion 15 fits the second attachment opening 10*b* with some clearance to allow for positional flexibility of the cassette 950 relative to the case 17, and to allow for an encapsulating material (e.g., epoxy) 11*a* to further secure the cassette 950 to the case 17. The second attachment portion 15 is preferably configured as a cylindrical post. However, other shapes and configurations of the second attachment portion may be employed as suitable to ensure a proper alignment and connection between the cassette and the case. For example, the cassette may be connected to the case with a single snap fit type attachment portion as an alternative to the two posts shown in the figures.

Figures 11A, 11B, 11C, 11D:
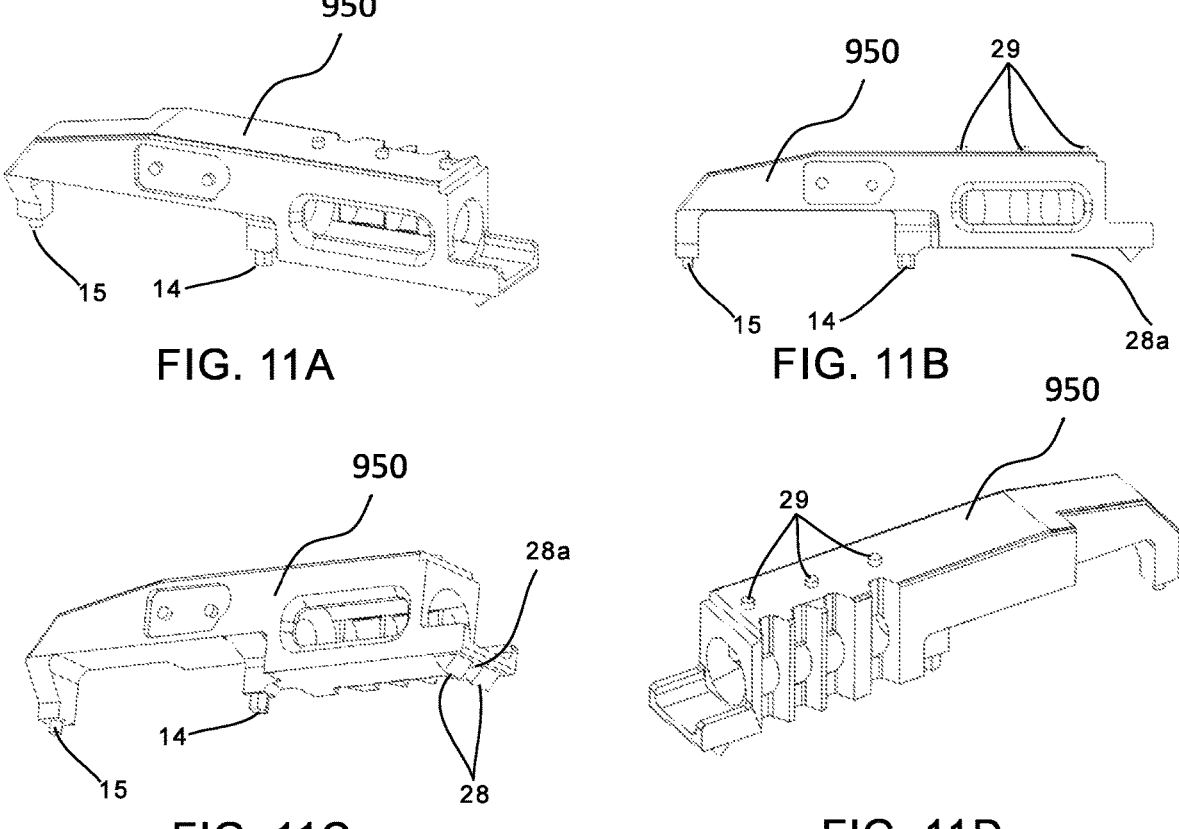
FIG. 11A-D are various views of an illustrative embodiment of a cassette to be employed with the IPG shown in FIG. 8.

As shown in FIG. 11C, the cassette 950 may also include support legs 28. The support legs 28 are configured to minimize the contact between the cassette and the case and provide for additional space including a gap 28*a* for encapsulating material 11*a* to flow under the cassette 950. The support legs are shown as a "v" shape in FIGS. 11A-11D, but conical or other appropriate shape may be employed. The cassette 950 may includes upper projections 29 which are configured to providing for positioning attachment to the antenna 16.

Figure 12A:
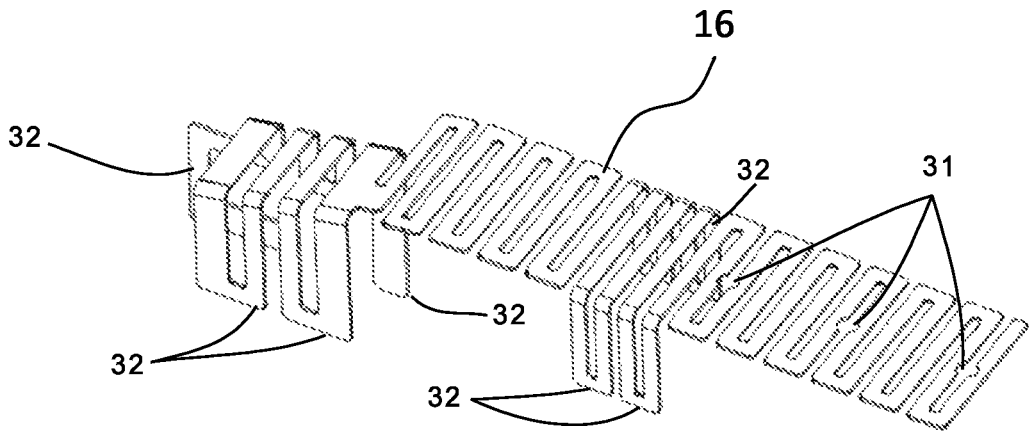
FIG. 12A is a perspective view of an illustrative embodiment of an antenna for an IPG shown in FIG. 8.
Figure 12B:
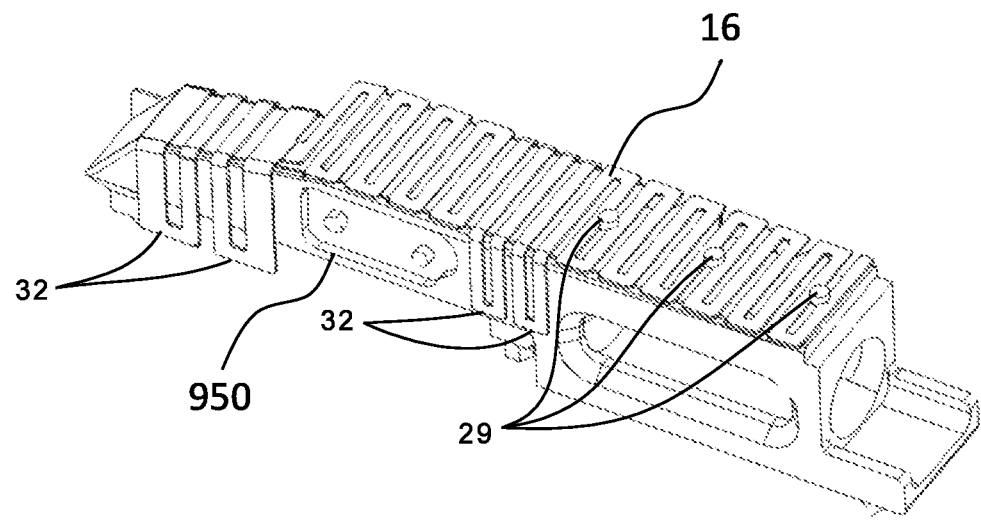
FIG. 12B is a perspective view of an illustrative embodiment of the antenna of FIG. 12A with the cassette shown in FIG. 11A-11.

FIG. 12A is a perspective view of the antenna 16 and FIG. 12B shows the antenna fitted onto the cassette. The antenna is an inverted F type antenna having projection openings 31 configured to be coupled to the upper projections 29 of the cassette 950. The antenna 16 may include one or more side wings 32 that extend downwardly along the cassette 950 to ensure stability and positioning of the antenna to the cassette 950. The antenna 16 may alternatively be any of a variety of antennas such as but not limited to other patch antennas and the like. Such antennas are those suitable for compact portable devices which may be designed for UHF and microwave frequencies among others.

Figure 13:
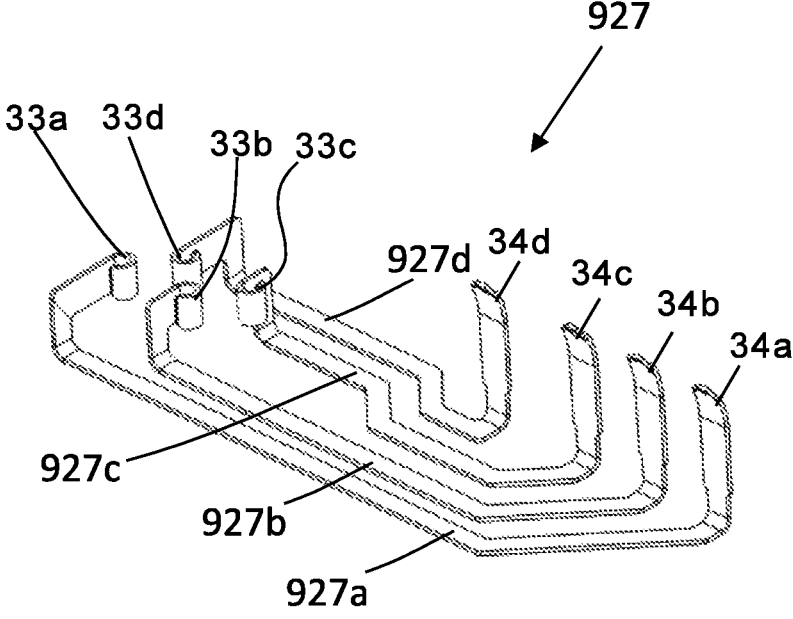
FIG. 13 is a perspective view of an illustrative embodiment of a lead frame to be employed with the IPG of FIG. 8.

FIG. 13 depicts the lead frame 927 which may include four leads. Each of leads is a conductor configured to form part of an electrode circuit of the IPG. The conductor leads 927*a*-927*d* may be configured as generally flat or planar and may be positioned to extend along the top surface of the case 17. At one end, each of the the conductor leads 927*a*-927*d* may be configured to bend upwardly and coil or wrap around one of the feedthrough pins to increase the surface area of the lead frame conductor in contact with the feedthrough pin. For example, as shown in FIG. 13, each of the leads 927*a*-927*d* may include a curved end 33*a*-33*d* cylindrically coiled to wrap around one of feedthrough pins. At the other end of the lead frame, each of the conductor leads 927*a*-927*d* may be configured to make electrical contact with a corresponding connector 919 or end cap 921 of the connector stack. Each conductor leads may include ends 34*a*-34*d* that bend upwardly to make contact with a corresponding connector 919 and the end cap 921. The lead frame may be welded at one end to the feedthrough pins and at the other end to the connector stack to ensure the electrical connections are secure.

Figure 14:
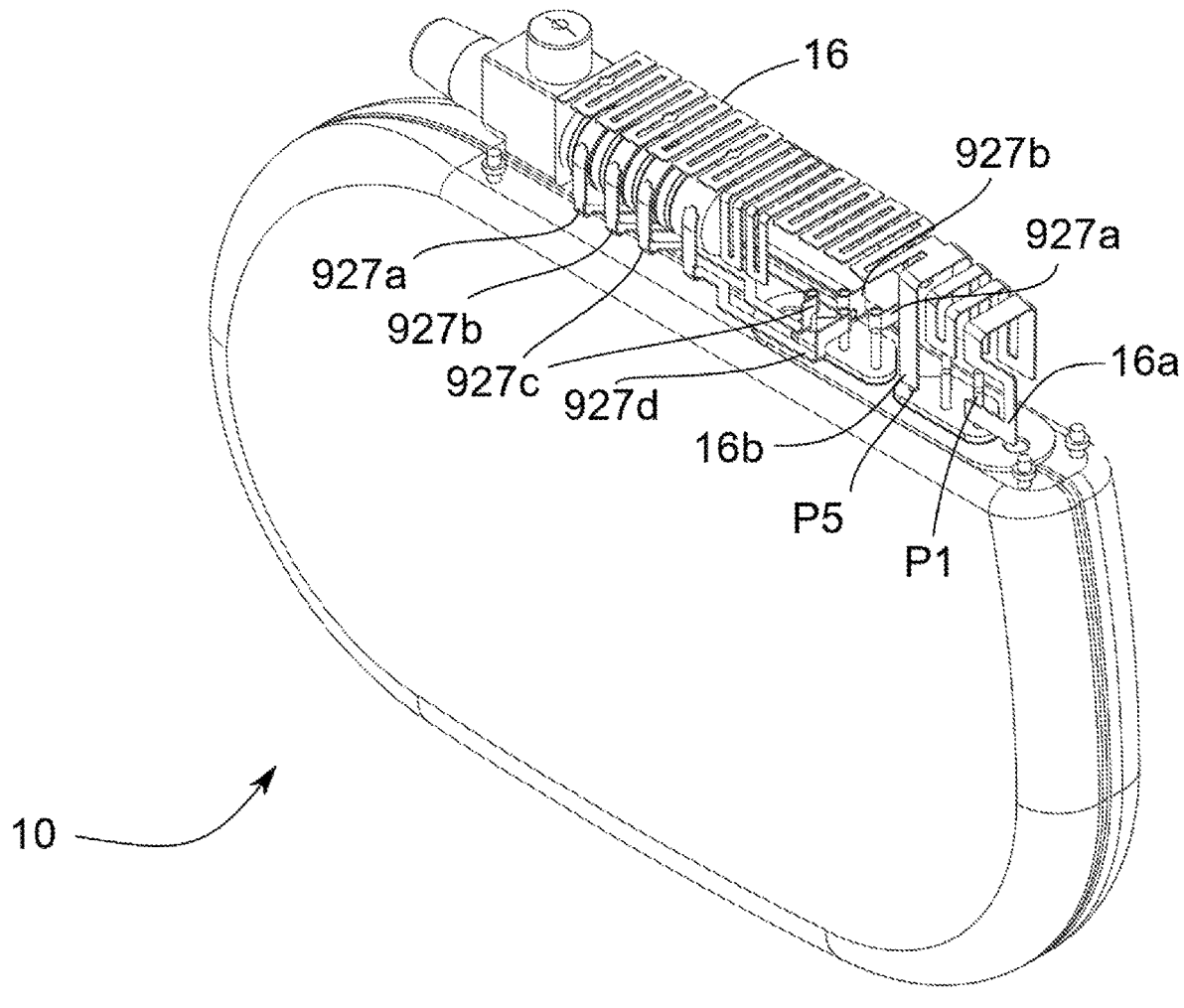
FIG. 14 is a perspective view of an illustrative embodiment of an IPG shown in FIG. 10 showing the antenna and the lead frame.

FIG. 14 depicts an exemplary connection of the antenna 16 and the lead frame 927 onto the feedthrough pins with the cassette omitted in order to improve visibility of the connection between the various electrical conductors. The antenna 16 may include a shorting arm 16*a* connected to one of the feedthrough pins (e.g., P1) and a feed arm 16*b* connected to another one of the feedthrough pins (e.g., P5). The connections between the antenna 16 and the feedthrough pins may be welded connections in order to ensure secure electrical connections. As shown in FIG. 14, the conductor leads 927*a*-927*b* may each be connected to one of the feedthrough pins. For example, lead 927*a* may be configured to connect to pin P8, conductor lead 927*b* may be configured to connect to pin P10, conductor lead 927*c* may be configured to connect to pin P11, and conductor lead 927*d* may be configured to connect to pin P9. The arrangement of and the number of the conductor leads 927*a*-927*d* and/or pins P8-P11 may be modified or altered as necessary depending upon the configuration of the IPG circuitry and the output of the pulse control module 604.

Components or parts of embodiments described herein are exemplary and other known components or known designs to one or ordinary skill in the art may be utilized.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

It is important to note that the construction and arrangement of the neurostimulator as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments.

Other substitutions, modifications, changes and omissions may also be made in the design, operating conditions and arrangement of the various exemplary embodiments without departing from the scope of the present disclosure.

What is claimed is:

1. An implantable pulse generator (IPG), comprising:
a case containing an energy storage device;
a header coupled to the case, the header including:
    a cassette having a plurality of upper projections;
    an antenna coupled to the cassette and having projection openings on a top surface of the antenna to be coupled to the plurality of upper projections of the cassette, the antenna having side wings that extend along the cassette, the side wings bent at least partially around the cassette and electrically coupled to the case, the case configured as a part of the antenna for receiving and transmitting electromagnetic signals; and
    an electrode attachment structure configured to couple with the cassette and configured to couple with one or more electrode leads.

2. The IPG of claim 1, wherein the case includes a connector plate having a first set of pins and a second set of pins.

3. The IPG of claim 2, wherein the header further includes a lead frame coupled to the cassette, the lead frame coupling the electrode leads to the second set of pins.

4. The IPG of claim 3, wherein the first set of pins are configured to couple to the antenna and protrude into the header.

5. The IPG of claim 4, wherein the electrode attachment structure includes a strain relief, and a set screw block.

6. The IPG of claim 3, wherein the antenna includes a patch antenna.

7. The IPG of claim 3, wherein the header includes an X-Ray Identification element.

8. The IPG of claim 3, wherein the header includes a fill material for sealing the header.

9. The IPG of claim 8, wherein the fill material includes an epoxy material.

10. The IPG of claim 3, wherein the antenna is electrically coupled to the case by at least one capacitor.

11. The IPG of claim 3, wherein the antenna is configured to be bent around the cassette.

12. The IPG of claim 4, wherein the antenna is coupled to the cassette by at least one pin on the cassette.

13. The IPG of claim 3, wherein the antenna includes an inverted-F type antenna.

14. A header for an implantable biomedical device, comprising:
a cassette providing a support structure and having a plurality of upper projections;
an antenna coupled to the cassette and having projection openings on a top surface of the antenna configured to be coupled to the plurality of upper projections of the cassette, the antenna having side wings that extend along the cassette, the side wings bent at least partially around the cassette and configured to be electrically coupled to a case of the implantable biomedical device, the case configured as a part of the antenna for receiving and transmitting electromagnetic signals; and
an electrode attachment structure configured to couple with the cassette and configured to couple with the one or more electrode leads.

15. The header of claim 14, wherein the header is configured to receive a first and second set of feedthrough pins from a case of the implantable biomedical device.

16. The header of claim 15, wherein the header further includes a lead frame coupled to the cassette, the lead frame coupling the electrode leads the second set of feedthrough pins.

17. The header of claim 15, wherein the header includes a plurality of apertures configured to receive the first set of feedthrough pins coupled to the case.

18. The header of claim 14, wherein the electrode attachment structure includes a strain relief, and a set screw block.

19. The header of claim 14, wherein the header includes a fill material for sealing the header.

20. The header of claim 19, wherein the header includes one or more holders configured to hold a mold for the fill material.

21. The header of claim 14, wherein the cassette includes a first attachment feature configured as a post to locate and couple with a complimentary first attachment feature on a case of the implantable biomedical device.

22. The header of claim 21, wherein the cassette includes a second attachment feature configured as a post to locate and couple with a complimentary second attachment feature on the case of the implantable biomedical device.

23. The header of claim 22, wherein the first attachment feature couples with the complimentary first attachment feature using an interference fit and the second attachment feature is configured to fit within the complimentary second attachment feature with clearance.

24. The header of claim 14, wherein the cassette includes at least one spacing feature configured to provide space between the cassette and a case of the implantable biomedical device.

25. The header of claim 14, wherein the cassette includes alignment features configured to enable alignment of lead contacts, coupled to one or more stimulation leads, with contacts of a lead frame.

26. An implantable pulse generator (IPG), comprising:
a case containing an energy storage device;
a header coupled to the case, the header including:
    a cassette providing a support structure having a plurality of upper projections;
    an antenna and having projection openings configured on a top surface of the antenna configured to be coupled to the plurality of upper projections of the cassette, the antenna having side wings that extend along the cassette, the side wings bent at least partially around the cassette and electrically coupled to the case through at least one capacitor, the case configured as a part of the antenna for receiving and transmitting electromagnetic signals;

an electrode attachment structure configured to couple with the cassette and configured to couple with one or more electrode leads; and an epoxy fill material for sealing the header.

* * * * *